United States Patent [19]

Christidis

[11] Patent Number: 4,948,827

[45] Date of Patent: Aug. 14, 1990

[54] METHYL-2-TERTIARY BUTYL-5-THIOPHENOL, ITS PREPARATION PROCESS AND ITS USE

[75] Inventor: Yani Christidis, Paris, France

[73] Assignee: Societe Francaise Hoechst, Puteaux, France

[21] Appl. No.: 426,607

[22] Filed: Oct. 25, 1989

[30] Foreign Application Priority Data

Nov. 8, 1988 [FR] France ................... 88 14572

[51] Int. Cl.$^5$ ............... C07C 149/32; C08C 19/20; C08K 5/37
[52] U.S. Cl. ................... 524/392; 525/350; 526/224; 568/67; 568/68
[58] Field of Search ............ 524/392; 525/350; 568/67, 68; 526/224

[56] References Cited

U.S. PATENT DOCUMENTS

| | | | |
|---|---|---|---|
| 2,064,580 | 12/1936 | Williams et al. ............... | 525/350 |
| 3,076,851 | 2/1963 | Neuworth . | |
| 3,960,824 | 6/1976 | Hicks ............................. | 526/224 |
| 3,984,609 | 10/1976 | Branlard et al. . | |
| 4,006,186 | 2/1977 | Engels et al. . | |
| 4,098,763 | 7/1978 | Stames ............................ | 524/392 |
| 4,555,541 | 11/1985 | Reid et al. . | |
| 4,619,957 | 10/1986 | Reid et al. . | |

FOREIGN PATENT DOCUMENTS

| | | |
|---|---|---|
| 0152097 | 2/1985 | European Pat. Off. . |
| 1274294 | 11/1960 | France . |
| 40-3975 | 3/1965 | Japan . |

OTHER PUBLICATIONS

Kuliev, E. M. et al.: CA 66 94763p (1967).
Chemical Abstracts, vol. 104, No. 8, Feb. 24, 1986, by the American Chemical Society, Colombus, Ohio, p. 568, resume No. 59416j, (JP-A-60 121 443, Sony Corp.), 28-06-1985.

*Primary Examiner*—Veronica P. Hoke
*Attorney, Agent, or Firm*—Browdy and Neimark

[57] ABSTRACT

This new thiophenol, prepared by reduction of tertiary butyl-4-toluenesulfonyl-2-chloride with the zinc-sulphuric acid couple, can be used as a stabilizer for vinyl chloride polymers, as a chain-transfer agent and as a peptizer.

4 Claims, No Drawings

METHYL-2-TERTIARY BUTYL-5-THIOPHENOL, ITS PREPARATION PROCESS AND ITS USE

The present invention relates to methyl-2-tertiobutyl-5 thiophenol, its preparation process and its use.

In the rubber industry as in the plastics industry, sulphur derivatives such as thiols, sulphides, etc. are currently used as plasticizers, peptizers, stabilizers or as chain-transfer agents in reactions of radical polymerization. Of these derivatives, alkylmercaptans, xylylmercaptans or alkylthiophenols and also their mercaptides are largely used. These sulphur derivatives, although active and economical, have a persistent and disagreeable intrinsic sulphurous odour, even in weak doses, which they communicate to the polymers containing them, which restricts their industrial uses and even prohibits their use in food packaging and notably in the manufacture of plastic bottles for table water.

Moreover, for some years equipment and/or food products prewrapped with plastic films have been treated with electromagnetic radiation in order to sterilize them, which necessitates the use of stabilized plastic packaging to prevent untimely decomposition. For a number of years efficient, economical and non-odorous stabilizers have been sought to respond to the needs of the market.

The applicant has surprisingly found that methyl-2 tertiary butyl-5 thiophenol, unlike other alkylated thiophenols, simultaneously exhibits excellent stabilizing properties for plastic films as well as good properties as a chain-transfer agent without having a disagreeable sulphurous odour, and especially without transmitting such odor during use.

Methyl-2 tertiobutyl-5 thiophenol is at 20° C. a colourless, transparent, fluid, refringent liquid, soluble in organic solvents and insoluble in water, with a refractive index of 1.5480 and with a citronella odour. It is not very sensitive to oxidizers, particularly to mineral peroxides such as the ammonium or alkali metal peroxodisulfates currently used as reaction primers in radical polymerization.

It is easily obtained by the reduction of tertiary butyl-4-toluenesulfonyl-2 chloride either by the zinc-sulphuric acid couple or by the iodhydric acid-red phosphorous couple.

The tertiary butyl-4 toluenesulfonyl-2 chloride starting material is cited in the literature in mixture with tertiobutyl-3-toluenesulfonyl-2-chloride (23/77 in weight). This mixture has a boiling point of 155° ±2° C. under 2.7 kPa (M. Tashiro et al, Org. Prep. Proced. Int. 1976, 8 (6) 249– 262). In the framework of the present invention tertiary butyl-4-toluenesulfonyl-2-chloride has been obtained by chlorosulfonation directly from paratertiary butyltoluene with chlorosulphonic acid in trichloroethylene according to the classical method (Wagner-Zook, Synthetic Organic Chemistry, method 550, p 822, Wiley, N.Y., 1953).

In its uses, particularly as a stabilizer of vinyl chloride polymers, methyl-2 tertiary butyl-5 thiophenol is generally used in amounts less than or equal to 5% by weight relative to the weight of the polymer. Usually, for a given use, particularly as a peptizer, and for an identical result, because of its great efficiency it is used in amounts less than those of similar products such as dodecylmercaptan, xylylmercaptans, alkylthiophenols (cf., for example, French Patent Nos. 1,274,294 and 1,339,458 and European Patent Application Nos. 84,882, 152,097 and 177,784) and it results each time in odourless end products. Thus, for example, when it is used as a chain-transfer agent in the radical polymerisation reaction of methyl acrylate, even though it is used at an amount of 4% by weight relative to the weight of the monomers, the polymer obtained is odourless whereas to obtain the same viscosity result it is necessary to use double the amount, namely 8% by weight relative to the weight of the monomers, of dodecylmercaptan and the polymer obtained is unusable because of its strong, sulphurous odour.

The following examples illustrate the invention without however limiting it.

EXAMPLE 1

700 g (6 mole) of chlorosulfonic acid is introduced over four hours at ambient temperature into an agitated solution of:

296.5 g (2 mole) of tertiary butyl-4-toluene, in 1460 g of trichloroethylene.

The temperature of the reaction medium remains between 20° C. and 32° C. and the hydrogen chloride given off is absorbed in wash bottles containing water.

After this the reaction medium is left under agitation at ambient temperature for 3 hours, then decanted, and the organic phase is poured under agitation into 2 kg of iced water. After decanting, it is washed with a saturated aqueous solution of sodium hydrogen carbonate until the wash water is obtained at pH 6 and it is then dried over anhydrous calcium chloride and finally the trichloroethylene is eliminated by distillation under vacuum. 461 g of oil is obtained which is distilled at 170°±2° C. under a vacuum of 300 Pa. In this way 419.5 g of tertiary butyl-4-toluenesulfonyl-2-chloride is isolated in the form of a mobile liquid.

|  | Microanalysis | |
|---|---|---|
|  | S % | Cl % |
| calculated | 13.00 | 14.37 |
| found | 13.00 | 14.4 |

EXAMPLE 2

500 g of finely powdered zinc is introduced rapidly at 90° C. and under agitation into 3700 g (2930 ml) of 11.6N sulphuric acid and then over 45 minutes, 493 g (2 mole) of tertiary butyl-4 toluenesulfonyl-2 chloride is introduced at boiling point into the suspension obtained.

The reaction medium is left for one hour at reflux, then cooled again to the ambient temperature. The product sought is extracted with toluene then the organic toluene phases are washed successively with water and then with a saturated aqueous solution of sodium hydrogen carbonate, and finally they are distilled under vacuum.

292 g (1.62 mole) of methyl-2 tertiary butyl-5 thiophenol is thus obtained which distils at 121°–122° C. under a vacuum of 1.9 kPa, namely a yield of 81% of the calculated theoretical value relative to the tertiary butyl-4 toluenesulfonyl-2 chloride used.

| NMR physical analysis of the proton (CDCl$_3$) | | | |
|---|---|---|---|
| 1.30 ppm | s | 9H | tertiobutyl |
| 2.30 ppm | s | 3H | methyl |
| 3.20 ppm | s | 1H | thiophenol |

| -continued | | | |
|---|---|---|---|
| NMR physical analysis of the proton (CDCl$_3$) | | | |
| 7-7.3 ppm | m | 3H | aromatics |

Physical analysis: chromatography in gaseous phase, homogeneous product.

| | Microanalysis | | |
|---|---|---|---|
| | C % | H % | S % |
| $C_{11}H_{16}S$ 180.31 calculated | 73.27 | 8.94 | 17.78 |
| found | 73.4 | 9.2 | 17.5 |

EXAMPLE 3

At ambient temperature:
320 g of methyl acrylate,
12.8 g of methyl-2 tertiary butyl-5 thiophenol, is emulsified in:
175 g of demineralised water,
8 g of Hostapal BV conc., marketed by the applicant,
3.2 g of nonylphenol polyethoxylated with 30 mole of ethylen oxide
1.6 g of sodium acetate,
6.4 g of ammonium peroxodisulfate.

This emulsion is then introduced over 2 hours under agitation into a solution held at 86°–88° C. and comprising:
200 g of demineralised water,
2.6 g of Hostapal BV. conc.,
then, when the addition is complete, heating is continued for 30 minutes at 88° C. and finally
317 g of sodium hydroxide at 47% by weight,
is introduced over 90 minutes at this temperature and the methanol formed is distilled off. When 50 g of the distillate has been obtained, the reaction medium is cooled to the ambient temperature. 1000 g of an aqueous solution of sodium polyacrylate at 40% by weight is thus obtained, having a Brookfield viscosity RVT, at rate 100, of 200 mPa.s and without odour.

It is clear that the present invention has been described only in a purely illustrative manner and is not at all limiting and that any modification could be introduced, particularly as regards equivalences, without departing from it.

I claim:
1. Methyl-2 tertiary butyl-5 thiophenol.
2. In a method of stabilizing a vinyl chloride polymer with a stabilizer, the improvement wherein said stabilizer is 2-methyl 5-tertiary butyl thiophenol.
3. In a method of controlling molecular weight of a polymer with a chain transfer agent, the improvement wherein said chain transfer agent is 2-methyl 5-tertiary butyl thiophenol.
4. In a method of peptizing a rubber with a peptizer, the improvement wherein said peptizer is 2-methyl 5-tertiary butyl thiophenol.

* * * * *